US008304616B2

(12) United States Patent
Boerma et al.

(10) Patent No.: US 8,304,616 B2
(45) Date of Patent: Nov. 6, 2012

(54) SOYBEAN VARIETY G00-3209

(75) Inventors: H. Roger Boerma, Athens, GA (US);
Richard S. Hussey, Athens, GA (US);
Daniel V. Phillips, Hendersonville, NC (US); Edwin Dale Wood, Winterville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 307 days.

(21) Appl. No.: 12/756,120

(22) Filed: Apr. 7, 2010

(65) Prior Publication Data
US 2010/0257631 A1    Oct. 7, 2010

Related U.S. Application Data

(60) Provisional application No. 61/167,468, filed on Apr. 7, 2009.

(51) Int. Cl.
| A01H 1/00 | (2006.01) |
| A01H 4/00 | (2006.01) |
| A01H 5/00 | (2006.01) |
| A01H 5/10 | (2006.01) |
| C12N 15/82 | (2006.01) |

(52) U.S. Cl. ........ 800/312; 800/260; 800/263; 800/264; 800/265; 800/279; 800/281; 800/284; 800/286; 800/300; 800/301; 800/302; 435/415; 435/426; 435/430

(58) Field of Classification Search .................. None
See application file for complete search history.

(56) References Cited

U.S. PATENT DOCUMENTS

| 4,769,061 A | 9/1988 | Comai |
| 4,810,648 A | 3/1989 | Stalker |
| 4,940,835 A | 7/1990 | Shah et al. |
| 4,975,374 A | 12/1990 | Goodman et al. |
| 4,992,375 A | 2/1991 | Wright |
| 5,015,580 A | 5/1991 | Christou et al. |
| 5,024,944 A | 6/1991 | Collins et al. |
| 5,322,783 A | 6/1994 | Tomes et al. |
| 5,416,011 A | 5/1995 | Hinchee et al. |
| 5,530,191 A | 6/1996 | Maliga |
| 5,563,055 A | 10/1996 | Townsend et al. |
| 5,569,834 A | 10/1996 | Hinchee et al. |
| 5,684,242 A | 11/1997 | Schnable et al. |
| 5,879,903 A | 3/1999 | Strauch et al. |
| 6,040,497 A | 3/2000 | Spencer et al. |
| 6,140,556 A | 10/2000 | Conway |
| 6,762,344 B1 | 7/2004 | Spencer et al. |
| 7,645,923 B1 | 1/2010 | Stephens et al. |
| 7,649,127 B2 | 1/2010 | Eby |
| 7,687,686 B2 | 3/2010 | Owen |
| 7,767,887 B2 * | 8/2010 | Dougherty .................... 800/312 |
| 2003/0135879 A1 | 7/2003 | Weeks et al. |

FOREIGN PATENT DOCUMENTS

| EP | 0616644 | 9/1994 |
| EP | 1534858 | 6/2005 |
| WO | WO 91/13972 | 9/1991 |
| WO | WO 92/17598 | 10/1992 |
| WO | WO 93/11245 | 6/1993 |
| WO | WO 94/00992 | 1/1994 |
| WO | WO 2004/001063 | 12/2003 |

OTHER PUBLICATIONS

Abe, et al. 1987. "Molecular Cloning of a Cysteine Proteinase Inhibitor of Rice (Oryzacystatin)." *The Journal of Biological Chemistry* 262(35):16793-16797.
Allard, R.W. 1960. "Selection Under Self-Fertilization." *Principles of Plant Breeding*. Davis, California: John Wiley & Sons, NY, University of California, pp. 50-98.
Arondel, et al. 1992. "Map-Based Cloning of a Gene Controlling Omega-3 Fatty Acid Desaturation in *Arabidopsis*." *Science* 258(5086):1353-1355.
Beachy, Roger N. 1990. "Coat Protein-Mediated Resistance Against Virus Infection." 1990. *Annu. Rev. Phytopathol.* 28:451-474.
Boerma, et al. 2000. "Registration of 'Boggs' Soybean." *Crop Sci.* 40:294-295.
Bowers, et al. 1992. "Inheritance of Resistance to Soybean Mosaic Virus in 'Buffalo' and HLS Soybean." *Crop Sci.* 32:67-72.
Brim and Stuber. 1973. "Application of Genetic Maile Sterility to Recurrent Selection Schemes in Soybeans." *Crop Sci.* 13:528-530.
Carter, et al. 2003. "Registration of 'N7001' Soybean." *Crop Sci.* 43:1126-1127.
Chee and Slightom. 1995. "Transformation of Soybean (*Glycine max*) via *Agrobacterium tumefaciens* and Analysis of Transformed Pleants." *Methods Mol Biol.* 44:101-119.
Christianson, et al. 1983. "A Morphogenetically Competent Soybean Suspension Culture." *Science* 222(4624):632-634.
Day, et al. 2009. "Georgia 2009 Soybean, Sorghum Grain and Silage, Summer Annual Forages, and Sunflower Performance Tests." *The Georgia Agricultural Experiment Stations*, Annual Publication 103.
DeGreef, et al. 1989. "Evaluation of Herbicide Resistance in Transgenic Crops Under Field Conditions." *Bio/Technology* 7:61-64.
Don and Pemberton. 1981. "Properties of Six Pesticide Degradation Plasmids Isolated from *Alcaligenes paradoxus* and *Alcaligenes eutrophus.*" *J Bacteriol* 145(2):681-686.
Don, et al. 1985. "Transposon Mutagenesis and Cloning Analysis of the Pathways for Degradation of 2, 4-dichlorophenoxyacetic Acid and 3-chlorabenzoate in *Alcaligenes eutrophus* JMP134(pJP4)." *Juornal of Bacteriology* 161(1):85-90.
Evans, et al. 1971. "Bacterial Metabolism of 2,4-Dichlorophenoxyacetate." *Biochem J* 122:543-551.
Fisher, et al. 1993. "Starch Branching Enzyme II from Maize Endosperm." *Plant Physiology* 102(3):1045-1046.

(Continued)

*Primary Examiner* — Cynthia Collins
(74) *Attorney, Agent, or Firm* — Davis Wright Tremaine LLP

(57) ABSTRACT

Embodiments of the invention relate to the new soybean variety designated G00-3209 as well as the seeds, plants and derivatives of the new soybean variety G00-3209. Also provided are tissue cultures of the new soybean variety G00-3209 and the plants regenerated therefrom. Additional embodiments of the invention are directed to methods for producing soybean plants by crossing the new soybean variety G00-3209 with itself or another soybean variety and plants produced by such methods.

25 Claims, No Drawings

OTHER PUBLICATIONS

Fox, et al. 1993. "Stearoyl-Acyl Carrier Protein Δ9 Desaturase from *Ricinus communis* is a Diiron-Oxo Protein." *PNAS* 90(6):2486-2490.

Geiser, et al. 1986. "The Hypervariable Region in the Genes Coding for Entomopathogenic Crystal Proteins of *Bacillus thuringiensis*: Nucleotide Sequence of the *kurhd1* Gene of Subsp. *Kurstaki* HD1." *Gene* 48:109-118.

Hammock, et al. 1990. "Expression and Effects of the Juvenile Hormone Esterase in a Baculovirus vector." *Nature* 344:458-461.

Hayes, et al. 1992. "Molecular Cloning and Heterologous Expression of a cDNA Encoding a Mouse Glutathione S-transferase Yc Subunit Possessing High Catalytic Activity for Aflatoxin $B_1$-8,9-epoxide." *Biochem. J.* 285:173-180.

Linthorst, et al. 1993. "Nucleotide Sequence of a cDNA Clone Encoding Tomato (*Lycopersicon esculentum*) Cysteine Proteinase." Plant Physiol. 101:705-706.

Johnson and Bernard. 1963. "Soybean genetics and breading." In: *The Soybean*. Norman (ed) New York: Academic Press, pp. 1-73.

Jones, et al. 1994. "Isolation of the Tomato Cf-9 Gene for Resistance to *Cladosporium fulvum* by Transposon Tagging." *Science* 266(5186):789-793.

Kiihl, et al. 1977. "Grafting as a Tool in Soybean Breeding." *Crop Sci.* 17:181-182.

Kirihara, et al. 1988. "Differential Expression of a Gene for a Methionine-rich Storage Protein in Maize." *Mol Gen Genet* 211:477-484.

Klee, et al. 1985. "Vectors Transformation of Higher Plants." *Bio. Tech.* 3:637-642.

Knutzon, et al. 1992. "Modification of *Brassica* Seed Oil by Antisense Expression of a Stearoyl-Acyl Carrier Protein Desaturase Gene." *PNAS* 89(7):2624-2628.

Lazzeri, Paul A. 1995. "Stable Transformation of Barley via Direct DNA Uptake." *Methods Mol Biol.* 49:95-106.

Marcotte, et al. 1988. "Regulation of a Wheat Promoter by Abscisic Acid in Rice Protoplasts." *Nature* 335:454-457.

Martin, et al. 1993. "Map-based Cloning of a Protein Kinase Gene Conferring Disease Resistance in Tomato." *Science* 262(5138):1432-1436.

Miki, et al. 1990. "Transformation of *Brassica napus* canola cultivars with *Arabidopsis thaliana* acetohydroxyacis synthase genes and analysis of herbicide resistance." *Theoretical and Applied Genetics* 80:449-458.

Muller, et al. 2006. "Purification and Characterization of Two Enantioselective {alpha}—Ketoglutarate-Dependent Dioxygenases, RdpA and SdpA, from Sphingomonas Herbicidovorans MH." *Appl. Environ. Microbiol.* 72(7):4853-4861.

Nickell and Bernard. 1992. "Registration of L84-5873 and L84-5932 Soybean Germplasm Lines Resistant to Brown Stem Rot." *Crop Sci.* 32:835.

Parker, et al. 1946. "Action Spectrum for the Photoperiodic Control of Floral Initiation of Short-Day Plants." *Botanical Gazette* 108(1):1-26.

Poehlman and Sleper. 1995. "Breeding Field Crops" Ames, Iowa: Iowa State University Press.

Potrykus, et al. 1985. "Molecular and General Genetics of a Hybrid Foreign Gene Introduced Into Tobacco by Direct Gene Transfer." *Mol. Gen. Genet.* 199:169-177.

Przibilla, et al. 1991. "Site-Specific Mutagenesis of the D1 Subunit of Photosystem II in Wild-Type *Chlamydomonas*." *Plant Cell* 3(2):169-174.

Raboy, et al. 2000. "Origin and Seed Phenotype of Maize *low phytic acid* 1-1 and *low phytic acid* 2-$1^1$." *Plant Physiology* 124:355-368.

Sorgaard, et al. 1993. "Site-directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α-Amylase 1." *J Biol Chem* 268(30):22480-22484.

Shiroza, et al. 1988. "Sequence Analysis of the *Streptococcus mutans* Fructosyltransferase Gene and Flanking Regions." *J Bacteriol* 170(2):810-816.

Sneep and Hendriksen. 1979. "Current Breeding Methods." Wageningen (ed.), Center for Agricultural Publishing and Documentation 104-139.

Sprague and Dudley, eds. 1988. *Corn and Improvement, $3^{rd}$ edition*.

Tavladoraki, et al. 1993. "Transgenic Plants Expressing a Functional Single-chjain Fv Antibody are Specifically Protected from Virus Attack." *Nature* 366:469-472.

Uchimiya, et al. 1986. "Expression of a Foreign Gene in Callus Derived from DNA-treated Protoplasts of Rice (*Oryza sativa* L.)." *Mol. Gen. Genet.* 204:204-207.

Van Hartingsveldt, et al. 1993. "Cloning, characterization and overexpression of the phytase-encoding gene (*phy*A) of *Aspergillus niger*." *Gene* 127:87-94.

Walker, et al. 1979. "Comparison of Emasculation and Nonemasculation for Hybridization of Soybeans." *Crop Sci.* 19:285-286.

\* cited by examiner

SOYBEAN VARIETY G00-3209

PRIORITY CLAIM

The application claims priority of U.S. Provisional Application Ser. No. 61/167,468 (entitled "SOYBEAN VARIETY G00-3209", filed on Apr. 7, 2009), which is incorporated herein by reference in its entirety.

FIELD OF THE INVENTION

The invention disclosed herein generally relates to the field of soybean breeding. In particular, the invention relates to the novel soybean variety G00-3209.

BACKGROUND

There are numerous steps in the development of any novel, desirable plant germplasm. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in compositional traits.

Soybean, *Glycine max* (L), is an important and valuable field crop. Thus, a continuing goal of plant breeders is to develop stable, high yielding soybean varieties that are agronomically sound. The reasons for this goal are to maximize the amount of grain produced on the land used and to supply food for both animals and humans. To accomplish this goal, the soybean breeder selects and develops soybean plants that have the traits that result in superior varieties.

SUMMARY OF THE INVENTION

Embodiments of the invention are directed to a seed of the new soybean variety G00-3209. Embodiments of the invention also relate to a plant of the new soybean variety G00-3209 as well as a plant produced by growing the seed of the new soybean variety G00-3209. Such embodiments also include the derivatives of such plants.

Embodiments of the invention also relate to a tissue culture of regenerable cells of the new soybean variety G00-3209, as well as plants regenerated therefrom, wherein the regenerated soybean plant is capable of expressing all the physiological and morphological characteristics of a plant grown from the seed of the new soybean variety G00-3209. In some embodiments, the regenerable cells are from embryos, meristematic cells, pollen, leaves, roots, root tips, anther, pistil, flower, seed, boll, cotyledon, hypocotyl, shoot, protoplasts or stem of the new soybean variety G00-3209.

In embodiments of the invention, a soybean plant comprising a single locus conversion of the new soybean variety G00-3209 is provided, wherein the soybean plant is otherwise capable of expressing all the physiological and morphological characteristics of the new soybean variety G00-3209. In some embodiments, the single locus conversion includes a transgenic gene which has been introduced by genetic transformation into the new soybean variety G00-3209 or a progenitor thereof. In some embodiments, the single locus conversion can include a dominant or recessive allele. In some embodiments, the locus conversion can confer a desired trait upon the single locus converted plant, including herbicide resistance, insect resistance, resistance to bacterial, fungal, or viral disease, male fertility or sterility, and improved nutritional quality.

Embodiments of the invention are also directed to a first generation ($F_1$) hybrid soybean seed produced by crossing a plant of the new soybean variety G00-3209 to a second soybean plant. In some embodiments, the $F_1$ hybrid soybean plant is grown from the hybrid seed produced by crossing the new soybean variety G00-3209 to a second soybean plant. Embodiments of the invention also relate to a seed of an $F_1$ hybrid plant produced with the new soybean variety G00-3209 as one parent, the second generation ($F_2$) hybrid soybean plant grown from the seed of the $F_1$ hybrid plant, and the seeds of the $F_2$ hybrid plant.

In embodiments of the invention, a method of producing a plant of the new soybean variety G00-3209 comprising an added desired trait is provided, wherein the method includes introducing a transgene that confers a desired trait into a plant of the new soybean variety G00-3209. In some embodiments, the desired trait is selected from the group consisting of: male sterility, herbicide tolerance, insect or pest resistance, disease resistance, site-specific recombination, abiotic stress tolerance, modified phosphorus characteristics, modified antioxidant characteristics, modified essential seed amino acid characteristics, modified fatty acid metabolism, modified carbohydrate metabolism and modified soybean fiber characteristics. In some embodiments, the desired trait is the synthesis of a protein encoded by the introduced transgene. The transgene can encode, for example, a protein selected from the group consisting of phytase, fructosyltransferase, levansucrase, a-amylase, invertase and starch branching enzyme or encode an antisense of stearoyl-ACP desaturase.

In some embodiments, the desired trait is herbicide tolerance to an herbicide selected from the group consisting of: glyphosate, sulfonylurea, imidazalinone, dicamba, glufosinate, phenoxy proprionic acid, cycloshexone, triazine, benzonitrile, broxynil, and chlorophenoxy acetic acid.

In some embodiments, the desired trait is insect resistance, wherein the transgene encodes a *Bacillus thuringiensis* (Bt) endotoxin.

In embodiments of the invention, a method of producing soybean seeds is provided, the method including crossing a plant of the new soybean variety G00-3209 to a second soybean plant. In some embodiments, the second soybean plant is another G00-3209 plant. In some embodiments, the second soybean plant is the same G00-3209 plant. In some embodiments, the method of crossing includes the steps of: a) planting seeds of the new soybean variety G00-3209; b) cultivating soybean plants resulting from said seeds until said plants bear flowers; c) allowing fertilization of the flowers of said plants; and, d) harvesting seeds produced from said plants.

Embodiments of the invention also relate to a method of producing hybrid soybean seeds, wherein the method includes crossing the new soybean variety G00-3209 to a second, distinct soybean plant which is nonisogenic to the new soybean variety G00-3209. In some embodiments, the crossing includes the steps of a) planting seeds of the new soybean variety G00-3209 and a second, distinct soybean plant, b) cultivating the soybean plants grown from the seeds until the plants bear flowers; c) cross pollinating a flower on one of the two plants with the pollen of the other plant, and d) harvesting the seeds resulting from the cross pollinating.

Embodiments of the invention are directed to a method for developing a soybean plant in a soybean breeding program comprising: a) obtaining a soybean plant, or its parts, of the new soybean variety G00-3209; and b) employing said plant or parts as a source of breeding material using plant breeding techniques. In some embodiments, the plant breeding techniques can be selected from the group consisting of recurrent selection, mass selection, bulk selection, backcrossing, pedigree breeding, genetic marker-assisted selection and genetic transformation. In some embodiments, a plant of the new soybean variety G00-3209 is used as the male or female parent.

Embodiments of the invention also provide a method of producing a soybean plant derived from the new soybean variety G00-3209, the method including the steps of: a) preparing a progeny plant derived from the new soybean variety G00-3209 by crossing a plant of the G00-3209 with a second soybean plant, wherein a sample of the seed of the new soybean variety G00-3209 was deposited under ATCC Accession No. PTA-10783; and b) crossing the progeny plant with itself or a second plant to produce a progeny plant of a subsequent generation which is derived from a plant of the new soybean variety G00-3209. In some embodiments, the method further includes the steps of: (c) crossing the progeny plant of a subsequent generation with itself or a second plant; and (d) repeating steps (b) and (c) for at least 2-10 additional generations to produce an inbred soybean plant derived from the new soybean variety G00-3209.

In embodiments of the invention, a method of producing a soybean plant derived from the new soybean variety G00-3209 is provided, the method including: (a) crossing a soybean plant derived from the new soybean variety G00-3209 with itself or another soybean plant to yield additional soybean variety G00-3209-derived progeny soybean seed; (b) growing the progeny soybean seed of step (a) under plant growth conditions, to yield additional soybean variety G00-3209-derived soybean plants; and (c) repeating the crossing and growing steps of (a) and (b) from 0 to 7 times to generate further soybean variety G00-3209-derived soybean plants.

Embodiments of the invention also relate to a method of introducing a single locus conversion into the new soybean variety G00-3209, the method including: (a) crossing a plant of the new soybean variety G00-3209, representative seed of said soybean variety having been deposited under ATCC Accession No. PTA-10783, with a second plant comprising a desired single locus to produce $F_1$ progeny plants; (b) selecting $F_1$ progeny plants that have the single locus to produce selected $F_1$ progeny plants; (c) crossing the selected progeny plants with at least a first plant of the new soybean variety G00-3209 to produce backcross progeny plants; (d) selecting backcross progeny plants that have the single locus and physiological and morphological characteristics of the new soybean variety G00-3209 to produce selected backcross progeny plants; and (e) repeating steps (c) and (d) one or more times in succession to produce selected second or higher backcross progeny plants that comprise the single locus and the physiological and morphological characteristics of the new soybean variety G00-3209 when grown in the same environmental conditions. In some embodiments, the single locus confers a trait selected from the group of: male sterility; herbicide tolerance; insect or pest resistance; disease resistance; site-specific recombination, abiotic stress tolerance, modified phosphorus characteristics, modified antioxidant characteristics, modified essential seed amino acid characteristics, modified fatty acid metabolism; modified carbohydrate metabolism; and modified soybean fiber characteristics. In some embodiments, the single locus confers the ability to synthesize a protein encoded by a gene located within the single locus.

Embodiments of the invention also include a plant produced by any of the methods disclosed herein. In some embodiments, the plant can further be defined as including at least two of the traits of the new soybean variety G00-3209 as described herein.

In embodiments of the invention, a method of producing a commodity plant product is provided, the method including obtaining a plant of the new soybean variety G00-3209 or a part thereof and producing said commodity plant product therefrom. In some embodiments, the commodity plant product is a protein concentrate, a protein isolate, soybean hulls, meal, flour or oil.

DETAILED DESCRIPTION OF THE INVENTION

Embodiments of the invention relate to methods and composition relating to plants, seeds and derivatives of the new soybean variety G00-3209. The new soybean variety G00-3209 is a conventional, non-Roundup Ready®, Maturity Group (MG) VII (relative maturity approximately 7.9) line that exhibits superior yield performance when compared with other MG VII cultivars of similar maturity. In 19 environments, the new soybean variety G00-3209 averaged approximately 19% higher seed yield (approximately 8.1 bushels/acre) than comparison soybean variety Benning. The new soybean variety G00-3209 averaged approximately 14% greater seed yield (approximately 6.5 bushels/acre) than comparison variety Haskell-RR when evaluated in 15 environments. The new soybean variety G00-3209 matures approximately 2 days later than Benning and is similar in maturity to Haskell-RR. The new soybean variety G00-3209 has white flowers, a tawny pubescence and tan pod walls. The seeds of the new soybean variety G00-3209 have black hila and dull seed coats. The new soybean variety G00-3209 is resistant to southern root-knot nematode, race 3 of soybean cyst nematode, stem canker (caused by *Diaporthe phaseolorum* var.), and red crown rot (caused by *Calonectria pyrochroa*). The new soybean variety G00-3209 exhibits susceptibility to peanut root-knot nematode and most other races of soybean cyst nematode.

Definitions

Unless otherwise noted, terms are to be understood according to conventional usage by those of ordinary skill in the relevant art.

As used herein, the term "plant" includes plant cells, plant protoplasts, plant cells of a tissue culture from which soybean plants can be regenerated, plant calli, plant clumps, and plant cells that are intact in plants or parts of plants, such as pollen, flowers, seeds, pods, leaves, stems, and the like.

As used herein, the term "backcrossing" refers to a process in which a breeder repeatedly crosses hybrid progeny, for example a first generation hybrid ($F_1$), back to one of the parents of the hybrid progeny. Backcrossing can be used to introduce one or more single locus conversions from one genetic background into another.

As used herein, the term "Stem Canker" refers to a visual disease score from 1 to 9 comparing all genotypes in a given test. The score is based on the number of dead plants caused by stem canker. A score of 0 indicates no dead plants. Visual scores range to a score of 9 which indicates severe symptoms resulting in 90 to 100% dead plants.

As used herein, the term "Red Crown Rot" refers to a visual disease score from 1 to 9 comparing all genotypes in a given test. The score is based on the number of dead plants caused by red crown rot. A score of 0 indicates no dead plants. Visual scores range to a score of 9 which indicates severe symptoms resulting in 90 to 100% dead plants.

As used herein, the term "Southern Root-knot Nematode" refers to a disease score from 1 to 5 comparing all genotypes in a given test. The score is based on a count of the number of southern root-knot nematode galls found on the roots of a plant. A score of 1 indicates there are few galls on the roots. The scores range to a score of 5 which indicates there are many galls.

As used herein, the term "Peanut Root-knot Nematode" refers to a disease score from 1 to 5 comparing all genotypes in a given test. The score is based on a count of the number of peanut root-knot nematode galls found on the roots of a plant. A score of 1 indicates there are few galls on the roots. The scores range to a score of 5 which indicates there are many galls.

As used herein, the term "crossing" refers to the mating of two parent plants.

As used herein, the term "cross-pollination" refers to fertilization by the union of two gametes from different plants.

As used herein, the term "emasculate" refers to the removal of plant male sex organs or the inactivation of the organs with a cytoplasmic or nuclear genetic factor conferring male sterility or a chemical agent.

As used herein, the term "emergence" refers to a score indicating the ability of a seed to emerge from the soil after planting. Each genotype is given a 1 to 9 score based on its percent of emergence. A score of 1 indicates an excellent rate and percent of emergence, an intermediate score of 5 indicates average ratings and a 9 score indicates a very poor rate and percent of emergence.

As used herein, the term "$F_1$ hybrid" refers to the first generation progeny of the cross of two nonisogenic plants.

As used herein, the term "marker" refers to a readily detectable phenotype, preferably inherited in codominant fashion (both alleles at a locus in a diploid heterozygote are readily detectable), with no environmental variance component, i.e., heritability of 1.

As used herein, the term "maturity date" encompasses the evaluation of plants considered as mature when about 95% of the pods have reached their mature color. The maturity date is typically described in measured days after August 31 in the northern hemisphere.

As used herein, the term "plant height" refers to the measurement taken from the top of soil to the top node of the plant and is typically measured in inches.

As used herein, the term "lodging" refers to the visual rating of the uprightness of the plants. The score is based on the average of the plants in a plot with a score of 1 indicating all plants are erect. The scores range to 5 where over about 80% of the plants in a plot are prostrate.

As used herein, the term "seed quality" refers to the visual rating of the completeness of the seed. The score is based on the completeness of the seed coat and overall soundness of the seed with a score of 1 indicating good quality seed. The scores range to 5 where the seeds are of poor quality.

As used herein, the term "regeneration" refers to the development of a plant from tissue culture.

As used herein, the term "relative maturity" refers to the maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

As used herein, the term "seed yield" refers to the yield in bushels/acre (bu/a) and is the actual yield of the grain at harvest.

As used herein, the term "self-pollination" refers to the transfer of pollen from the anther to the stigma of the same plant.

As used herein, the term "shattering" refers to the amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

As used herein, the term "single locus converted (conversion) plant" refers to plants which are developed by a plant breeding technique called backcrossing, wherein essentially all of the desired morphological and physiological characteristics of a soybean variety are recovered in addition to the characteristics of the single locus transferred into the variety via the backcrossing technique and/or by genetic transformation.

As used herein, the term "substantially equivalent" refers to a characteristic that, when compared, does not show a statistically significant difference (e.g., p=0.05) from the mean.

As used herein, the term "tissue culture" refers to a composition comprising isolated cells of the same or a different type or a collection of such cells organized into parts of a plant.

As used herein, the term "transgene" refers to a genetic locus comprising a sequence which has been introduced into the genome of a soybean plant by transformation.

Pedigree and History of the New Soybean Variety G00-3209

The new soybean variety G00-3209 was developed from a cross of N7001 (Carter et al. 2003. *Crop Sci.* 43:1126-1127, which is incorporated herein by reference in its entirety) and Boggs (Boerma et al. 2000. *Crop Sci.* 40:294-295, which is incorporated herein by reference in its entirety), which was conducted in the summer of 1995. N7001 was developed from the cross N77-114×PI 416937, wherein N77-114=Essex×N70-2173 and N70-2173=Hampton×Ransom.

The $F_1$ plants from the cross of N7001×Boggs were grown in Puerto Rico (the USDA-ARS Puerto Rican Lighted Soybean Nursery) during the winter of 1996 (Table 1). The $F_2$ generation was grown in the vicinity of Athens, Ga. (the University of Georgia Plant Sciences Farm, or "Plant Sciences Farm") in the summer of 1996. At maturity, 400 individual $F_2$ plants were threshed to produce $F_{2:3}$ lines. These lines were screened during the winter of 1997 for resistance to race 3 of soybean cyst nematode (*Heterodera glycines*; also referred to as "SCN(R3)") and to southern root-knot nematode (*Meloidogne incognita*; also referred to as "SRKN"). In the summer of 1997, 50 $F_{2:3}$ lines identified as potentially resistant to both SCN(R3) and SRKN were planted at the Plant Sciences Farm. At maturity, 43 agronomically desirable $F_{2:3}$ lines were selected and nine random $F_3$ plants were threshed from each selected row. In the winter of 1998, the $F_{3:4}$ lines were screened for SCN(R3) and SRKN. A total of 52 $F_{3:4}$ lines that were resistant to both nematode species were planted at the Plant Science Farm in the summer of 1998. In the fall, 32 agronomically desirable rows were visually selected and a single pod was sampled from each plant in the selected rows. The $F_5$ and $F_6$ generations were grown in the Puerto Rican nursery and advanced by the single-seed-descent method during the winter of 1999. In the summer of 1999 the $F_7$ generation was grown at the Plant Sciences Farm. At maturity a total of 500 plants were pulled and threshed individually to create $F_{7:8}$ lines. In the winter of 2000 these lines were screened in the greenhouse for resistance to SCN (R3). A total of 319 SCN(R3) resistant $F_{7:8}$ lines were grown at the Plant Sciences Farm in the summer of 2000. At maturity 81 $F_{7:8}$ rows were visually selected and each row was individually harvested. Progeny row #3209 was designated G00-3209. From 2001 to 2004, the new soybean variety G00-3209 was evaluated for seed yield, agronomic performance, seed composition, and disease resistance in Georgia and across the southern USA in a total of 19 environments.

TABLE 1

Development of the new soybean variety G00-3209

| Season | Year | Activitiy |
|---|---|---|
| Summer | 1995 | Crossed N7001 × Boggs |
| Winter | 1996 | Grew $F_1$ in USDA-ARS Puerto Rican Winter Nursery |
| Summer | 1996 | Grew $F_2$ at Plant Sciences Farm (near Athens GA) |
| Winter | 1997 | Screened $F_{2:3}$ lines in greenhouse for SCN(R3) and SRKN |
| Summer | 1997 | Grew 50 $F_{2:3}$ rows at Plant Sciences Farm |
| Winter | 1998 | Screened $F_{3:4}$ lines in greenhouse for SCN(R3) and SRKN |
| Summer | 1998 | Grew 52 $F_{3:4}$ rows at Plant Sciences Farm |
| Winter | 1999 | Grew $F_5$ and $F_6$ in Puerto Rican Winter Nursery |
| Summer | 1999 | Grew $F_7$ at Plant Sciences Farm |
| Winter | 2000 | Screened $F_{7:8}$ lines in greenhouse for SCN(R3) |
| Summer | 2000 | Grew $F_{7:8}$ rows at Plant Sciences Farm and selected G00-3209 |
| Summer | 2001 | Evaluated in replicated yield tests at Athens and Plains GA |
| Summer | 2002 | Evaluated in replicated yield tests at 4 locations |
| Summer | 2003 | Evaluated in replicated yield test at 5 Regional Prelim locations |
| Summer | 2004 | Evaluated in replicated yield tests at 10 Regional Test locations |
| Summer | 2005 | Produced breeder seed |

Description and Comparison of the New Soybean Variety G00-3209 to Comparison Varieties The new soybean variety G00-3209 is a conventional, non-Roundup Ready®, Maturity Group VII (relative maturity 7.9) line. It matures approximately 2 days later than Benning and is similar in maturity to Haskell-RR (see Tables 2, 3, and 4). It averages approximately 22 g/kg and about 16 g/kg higher protein and about 5 g/kg and about 3 g/kg lower oil content than Benning and Haskell-RR, respectively (see Table 6). The new soybean variety G00-3209 has white flowers, a tawny pubescence, and tan pod walls. Its seed have black hila and dull seed coats. It is resistant to SRKN, SCN(R3), stem canker (caused by *Diaporthe phaseolorum* var. *meridionalis*), and red crown rot (caused by *Calonectria pyrochroa*) (see Table 7). It is susceptible to peanut root-knot nematode (*Meloidogyne arenaria*) and most other races of soybean cyst nematode.

The new soybean variety G00-3209 has been observed to be genetically stable and uniform. The new soybean variety G00-3209 can be reproduced by planting and growing seeds of the variety under self-pollinating or sib-pollinating conditions, as is known to those of skill in the agricultural arts. The new variety G00-3209 shows no variants other than what would normally be expected due to environment or that would occur for almost any characteristic during the course of repeated sexual reproduction. The results of an objective description and performance characteristics of the new variety G00-3209 as analyzed and compared to comparison varieties are presented in Tables 2-7. Those of skill in the art will recognize that these are typical values that may vary due to environment and that other values that are substantially equivalent are within the scope of the invention.

TABLE 2

Mean performance of the new soybean variety G00-3209 and comparison variety Benning in four environments located in Georgia and North Carolina (2002)

| Strain | Seed yield bu/a | Maturity date (MM/DD) | Plant height inches | Lodging rating[1] | Seed weight mg/seed | Seed quality rating[2] |
|---|---|---|---|---|---|---|
| G00-3209 | 47.4a[3] | 10/22 | 35 | 2.1 | 162 | 3.0 |
| Benning | 38.9b | 10/20 | 35 | 1.4 | 184 | 3.7 |

[1]Rating: 1 (all plants erect) to 5 (over 80% of plants prostrate).
[2]Rating: 1 (very good) to 5 (very poor).
[3]Means followed by a different letter are significantly different based on LSD (0.05)

TABLE 3

Mean performance of the new soybean variety G00-3209 and comparison varieties in five locations for the 2003 Regional Uniform Preliminary Test VII

| Strain | Seed yield bu/a | Maturity date (MM/DD) | Plant height inches | Lodging rating[1] | Seed weight mg/seed | Seed quality rating[2] |
|---|---|---|---|---|---|---|
| G00-3209 | 52.7a[3] | 10/21 | 34 | 2.0 | 146 | 1.5 |
| Benning | 47.4a | 10/19 | 33 | 2.0 | 164 | 1.8 |
| Haskell-RR | 49.1a | 10/22 | 40 | 2.4 | 151 | 1.6 |

[1]Rating: 1 (all plants erect) to 5 (over 80% of plants prostrate).
[2]Rating: 1 (very good) to 5 (very poor).
[3]Means followed by a different letter are significantly different based on LSD (0.05)

TABLE 4

Mean performance of the new soybean variety G00-3209 and comparison varieties in ten locations for the 2004 USDA-ARS Regional Test VII

| Strain | Seed yield bu/a | Maturity date (MM/DD) | Plant height inches | Lodging rating[1] | Seed weight mg/seed | Seed quality rating[2] |
|---|---|---|---|---|---|---|
| G00-3209 | 52.2a[3] | 10/23 | 38 | 2.8 | 138 | 1.5 |
| Benning | 42.8b | 10/20 | 40 | 3.7 | 133 | 1.6 |
| Haskell-RR | 44.6b | 10/21 | 40 | 3.1 | 138 | 1.7 |

[1]Rating: 1 (all plants erect) to 5 (over 80% of plants prostrate).
[2]Rating: 1 (very good) to 5 (very poor).
[3]Means followed by a different letter are significantly different based on LSD (0.05)

TABLE 5

Overall seed yield of the new soybean variety G00-3209 and comparison varieties

| Strain | Xtest 4 2002 (4)[1] bu/a | UPT7 2003 (5) bu/a | UT7 2004 (10) bu/a | Mean (15) bu/a | Mean (19) bu/a |
|---|---|---|---|---|---|
| G00-3209 | 47.4a[2] | 52.7a | 52.2a | 52.3a | 51.4a |
| Benning | 38.9b | 47.4a | 42.8b | 44.1b | 43.1b |
| Haskell-RR | — | 49.1a | 44.6b | 45.8b | — |

[1]Number of locations
[2]Means followed by a different letter within a column are significantly different based on LSD (0.05)

TABLE 6

Mean seed protein and seed oil of the new soybean variety G00-3209 and comparison varieties in the 2003 and 2004 USDA-ARS Uniform Soybean Tests - Group VII

| Strain | Protein (g/kg) | | | Oil (g/kg) | | |
|---|---|---|---|---|---|---|
| | 2003 | 2004 | Mean | 2003 | 2004 | Mean |
| G00-3209 | 428a[1] | 415a | 422a | 191b | 194a | 193b |
| Benning | 413a | 387b | 400b | 199a | 197a | 198a |
| Haskell-RR | 418a | 394b | 406b | 196ab | 195a | 196ab |

[1]Means followed by a different letter within a column are significantly different based on LSD (0.05)

TABLE 7

Mean disease ratings of the new soybean variety G00-3209 and comparison varieties for resistance to pests, parasites and disease (mean of 2 tests each)

| Strain | Southern root-knot nematode rating[1] | Peanut root-knot nematode rating[1] | Soybean cyst nematode race 3 reaction[2] | Stem canker rating[3] | Red crown rot rating[3] |
|---|---|---|---|---|---|
| G00-3209 | 1.0a[4] | 3.6b | R | 0.2a | 1.3a |
| Hartwig | 1.6a | 3.6b | R | — | — |
| Haskell | 1.5a | 1.8a | S | — | — |
| Haskell-RR | — | — | S | 0.5a | 2.4b |
| G93-9009 | 1.0a | 1.6a | R | — | — |
| CNS | 5.0b | 5.0c | S | — | — |
| Bossier | 5.0b | 2.8b | S | — | — |
| G81-2057 | — | — | — | 7.9c | 3.8c |
| Hutton | — | — | — | 4.3b | 1.0a |

[1]Rating: 1 (few galls) to 5 (many galls)
[2]Reaction: R = resistant, S = susceptible
[3]Rating: 0 (0% dead plants) to 9 (90 to 100% dead plants)
[4]Means followed by a different letter within a column are significantly different based on LSD (0.05)

As described herein, the new soybean variety G00-3209 has consistently yielded more than the USDA-ARS Group VII Uniform Test comparison varieties, Benning and Haskell RR. In 19 environments, the new soybean variety G00-3209 averaged approximately 19% higher seed yield (approximately 8.1 bu/a) than Benning, as illustrated in Table 5. The new soybean variety G00-3209 also averaged approximately 14% greater seed yield (approximately 6.5 bu/a) than Haskell-RR when evaluated in 15 environments. When the new soybean variety G00-3209 was evaluated along with 12 additional elite breeding lines and two comparison varieties (Benning and Haskell-RR) in the 2004 Uniform Regional Test VII, it was observed that G00-3209 was the highest yielding entry at 5 of the 10 locations.

Table 8 shows a regional summary of yield results of soybean variety G00-3209 and comparison varieties.

TABLE 8

Regional Summary of Early and Late-Planted Soybean Maturity Groups VII and VIII Variety Performance in Georgia, 2008-2009.
Regional Summary of Early and Late-Planted Soybean Maturity Groups VII and VIM Variety Performance in Georgia, 2008-2009

| | | Yield[1] | | | | | |
|---|---|---|---|---|---|---|---|
| | | South[2] | | North[3] | | Statewide[4] | |
| Company or Brand Name | Variety | 2009 | 2-Year Average | 2009 | 2-Year Average bu/acre | 2009 | 2-Year Average |
| AgSouth | G00-3209 | 64.4 | 64.3 | 55.7 | 50.8 | 61.5 | 59.8 |
| DynaGro | V76N9RR | 57.4 | 60.5 | 58.3 | 50.0 | 57.7 | 57.0 |
| UGA | G04-1618RR | 52.6 | 57.2 | 54.5 | 49.1 | 53.3 | 54.5 |
| NK | S78-G6 | 52.7 | 56.0 | 56.4 | 48.3 | 53.9 | 53.4 |
| SS | RT7270N | 60.5 | 59.1 | 56.3 | 48.1 | 59.1 | 55.4 |
| UGA | G04-2215RR | 58.1 | 60.3 | 54.5 | 47.6 | 56.9 | 56.1 |
| UGA | G03-1187RR | 56.4 | 57.5 | 52.4 | 47.6 | 55.0 | 54.2 |
| Asgrow | AG7501 | 57.8 | 59.9 | 55.4 | 47.3 | 57.0 | 55.7 |
| USG | 77U28 | 54.7 | 57.7 | 52.1 | 46.0 | 53.8 | 53.8 |
| Pioneer | 97M50 | 53.7 | 54.4 | 52.1 | 46.0 | 53.1 | 51.6 |
| AsGrow | DP7870RR | 56.8 | 56.2 | 50.5 | 46.0 | 54.7 | 52.8 |
| NK | S80-P2 | 55.2 | 55.9 | 53.5 | 45.9 | 54.6 | 52.5 |
| Asgrow | AG7502 | 57.3 | 57.3 | 51.0 | 45.9 | 55.2 | 53.5 |
| USG | 7732nRR | 54.1 | 55.2 | 52.1 | 45.8 | 53.4 | 52.1 |
| Asgrow | H7242RR | 54.3 | 54.2 | 50.3 | 45.5 | 53.0 | 51.3 |
| UGA | G04-3248RR | 50.8 | 52.3 | 50.6 | 45.1 | 50.7 | 49.9 |
| AgSouth | AGS 758RR | 53.8 | 55.7 | 50.3 | 45.1 | 52.6 | 52.2 |
| NK | S74-W6 | 53.9 | 55.9 | 49.2 | 44.9 | 52.3 | 52.2 |
| Progeny | P7208RR | 57.1 | 57.5 | 49.8 | 44.7 | 54.7 | 53.2 |
| UGA | G04-2414RR | 56.8 | 58.7 | 52.8 | 44.0 | 55.5 | 53.8 |
| Public Variety | Cook | 54.1 | 54.6 | 50.1 | 43.9 | 52.7 | 51.0 |
| Asgrow | DP7330RR | 56.4 | 57.1 | 50.0 | 43.9 | 54.3 | 52.7 |
| Public Variety | Motte | 50.1 | 51.7 | 46.1 | 43.4 | 48.8 | 48.9 |
| UGA | G07PR-443 | 53.8 | 52.3 | 49.5 | 43.0 | 52.4 | 49.2 |
| AgSouth | AGS Prichard RR | 50.8 | 52.4 | 51.4 | 42.9 | 51.0 | 49.2 |
| DynaGro | 35K73 | 56.2 | 55.8 | 48.2 | 42.7 | 53.5 | 51.4 |

TABLE 8-continued

Regional Summary of Early and Late-Planted Soybean Maturity
Groups VII and VIII Variety Performance in Georgia, 2008-2009.
Regional Summary of Early and Late-Planted Soybean Maturity
Groups VII and VIM Variety Performance in Georgia, 2008-2009

| | | Yield[1] | | | | | |
|---|---|---|---|---|---|---|---|
| | | South[2] | | North[3] | | Statewide[4] | |
| Company or Brand Name | Variety | 2009 | 2-Year Average | 2009 | 2-Year Average bu/acre | 2009 | 2-Year Average |
| SS | RT7999N | 53.7 | 53.2 | 50.0 | 41.9 | 52.4 | 49.4 |
| AgSouth | AGS Benning | 48.8 | 52.0 | 46.2 | 41.6 | 48.0 | 48.5 |
| Public Variety | Santee | 55.1 | 56.7 | 44.9 | 40.8 | 51.7 | 51.4 |
| UGA | G-Has(4)PHY-1 | 51.4 | 51.6 | 44.9 | 39.6 | 49.2 | 47.6 |
| UGA | G05-1200RR | 55.2 | . | 53.6 | . | 54.7 | . |
| UGA | G05-1209RR | 54.2 | . | 53.2 | . | 53.9 | . |
| UGA | G05-1481RR | 55.6 | . | 53.1 | . | 54.7 | . |
| UGA | G05-3758RR | 57.5 | . | 51.4 | . | 55.5 | . |
| SC | SC02-208RR | 52.8 | . | 51.2 | . | 52.3 | . |
| USG | 77S09 | 55.2 | . | 51.2 | . | 53.9 | . |
| UGA | G05-4237RR | 56.5 | . | 50.7 | . | 54.6 | . |
| UGA | G05-2505RR | 52.5 | . | 50.1 | . | 51.7 | . |
| UGA | G05-2468RR | 57.2 | . | 48.0 | . | 54.1 | . |
| AgSouth | AGS 747RR | 54.4 | . | 47.6 | . | 52.2 | . |
| UGA | G05-2324RR | 49.8 | . | 47.6 | . | 49.1 | . |
| AU | AU02-2814 | 54.4 | . | 46.8 | . | 51.9 | . |
| Public Variety | NC Raleigh | 55.8 | . | 44.6 | . | 52.0 | . |
| Average | | 54.9 | 56.1 | 50.9 | 45.2 | 53.5 | 52.5 |
| LSD at 10% Level | | 6.9 | 4.3 | 4.9 | 4.3 | 3.5 | 2.4 |
| Std. Err. of Entry Mean | | 18.6 | 16.0 | 10.1 | 14.1 | 12.0 | 11.5 |

E = Eligible for consideration for recommendation.
[1]Yields calculated at 13% moisture.
[2]Plains Late, Midville Early, Plains Early, Tifton Early - Maturity Groups VII & VIII.
[3]Griffin Late and Athens Early - Maturity Groups VII & VIII.
[4]All six locations - Maturity Groups VII & VIII.
Data complied from:
Day, J. L. A. E. Coy, and J. D. Gassett. 2009. Georgia 2009 Performance Tests: Soybean, Sorghum Grain and Silage, Summer Annual Forages, and Sunflower. The Georgia Agricultural Experiment Stations, Annual Publication 103 (December 2009).

Table 8 shows that new soybean variety G00-3209 yielded more than all the other comparison varieties in Georgia in year 2008-2009. As used herein, "early-planted" and "late-planted" refer to different planting dates which are at least two weeks apart at a specific environment. More information regarding the data in Table 8 can be found in Day et al. (2009, Georgia 2009 Performance Tests: Soybean, *Sorghum* Grain and Silage, Summer Annual Forages, and Sunflower, The Georgia Agricultural Experiment Stations, Annual Publication 103), which is incorporated herein by reference.

Breeding and Selection Methods

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location can be effective, whereas for traits with low heritability, selection can be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding is used to transfer one or a few favorable genes for a highly heritable trait into a desirable variety. This approach has been used extensively for breeding disease-resistant varieties (Bowers et al. 1992. *Crop Sci*. 32(1):67-72; Nickell and Bernard. 1992. *Crop Sci*. 32(3): 835, each of which are incorporated herein by reference in its entirety). Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

A difficult task is the identification of individuals that are genetically superior, because for most traits the true genotypic value can be masked by other confounding plant traits or environmental factors. One method of identifying a superior plant is to observe its performance relative to other experimental plants and to one or more widely grown standard varieties. Single observations can be generally inconclusive, while replicated observations provide a better estimate of genetic worth.

The goal of plant breeding is to develop new, unique and superior soybean varieties and hybrids. A plant breeder initially selects and crosses two or more parental lines, followed by repeated selfing and selection, producing many new genetic combinations. Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines that is developed, except possibly in a very gross and general fashion. For example, the same breeder cannot produce the same variety twice by using the exact same original parents and the same selection techniques.

The development of new soybean varieties involves the development and selection of soybean varieties, the crossing of these varieties and selection of progeny from the superior hybrid crosses. A hybrid seed is produced by manual crosses between selected male-fertile parents or by using male sterility systems. Hybrids can be identified by using certain single locus traits such as pod color, flower color, pubescence color or herbicide resistance which indicate that the seed is truly a hybrid. Additional data on parental lines as well as the phenotype of the hybrid can influence the breeder's decision whether to continue with the specific hybrid cross.

Pedigree breeding and recurrent selection breeding methods are used to develop varieties from breeding populations. Breeding programs combine desirable traits from two or more varieties or various broad-based sources into breeding pools from which varieties are developed by selfing and selection of desired phenotypes.

Pedigree breeding is commonly used for the improvement of self-pollinating crops. Two parents which possess favorable, complementary traits are crossed to produce an $F_1$. An $F_2$ population is produced by selfing one or several $F_1$'s. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent. The source of the trait to be transferred is called the donor or nonrecurrent parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Sufficient numbers of seeds are harvested to make up for those plants that did not germinate or produce seed.

Descriptions of other breeding methods that are commonly used for different traits and crops can be found in one of several reference books (e.g., Allard. 1960. *Principles of plant breeding*. Davis, California: John Wiley & Sons, NY, University of California, pp. 50-98; Simmonds. 1979. *Principles of crop improvement*. New York: Longman, Inc., pp. 369-399; Sneep and Hendriksen. 1979. "Plant breeding perspectives." Wageningen (ed.), Center for Agricultural Publishing and Documentation; Fehr. 1987. "Principles of variety development." *Theory and Technique* (Vol. 1) and *Crop Species Soybean* (Vol. 2). New York: Macmillian Publishing Company, Iowa State University, pp. 360-376).

Breeding Soybean Variety G00-3209

Embodiments of the invention relate to methods for crossing the new soybean variety G00-3209 with itself or a second plant and the seeds and plants produced by such methods. These methods can be used for propagation of the new soybean variety G00-3209, or can be used to produce hybrid soybean seeds and the plants grown therefrom. Hybrid soybean plants can be used by farmers in the commercial production of soy products or can be advanced in certain breeding protocols for the production of novel soybean varieties. A hybrid plant can also be used as a recurrent parent at any given stage in a backcrossing protocol during the production of a single locus conversion of the new soybean variety G00-3209.

In selecting a second plant to cross with the new soybean variety G00-3209 for the purpose of developing novel soybean varieties, it is typically desired to choose those plants which either themselves exhibit one or more selected desirable characteristics or which exhibit the desired characteristic(s) when in hybrid combination. Exemplary desired characteristics include, but are not limited to, seed yield, lodging resistance, emergence, seedling vigor, disease tolerance, maturity, plant height, high oil content, high protein content and shattering resistance.

Any time the new soybean variety G00-3209 is crossed with another different variety, first generation ($F_1$) soybean progeny are produced. The hybrid progeny are produced regardless of characteristics of the two varieties produced. As such, an $F_1$ hybrid soybean plant can be produced by crossing G00-3209 with any second soybean plant. The second soybean plant can be genetically homogeneous (e.g., inbred) or can itself be a hybrid. Therefore, embodiments of the invention also include any $F_1$ hybrid soybean plant produced by crossing the new soybean variety G00-3209 with a second soybean plant.

Soybean plants (*Glycine max* L.) can be crossed by either natural or mechanical techniques (see, e.g., Fehr. 1980. "Soybean." In: *Hybridization of Crop Plants*. Fehr and Hadley (eds). Madison, Wis.: Am. Soc. Agron., Crop Sci. Soc. Am., pp. 590-599). Natural pollination occurs in soybeans either by self pollination or natural cross pollination, which typically is aided by pollinating organisms. In either natural or artificial crosses, flowering and flowering time can be an important consideration. Soybean is a short-day plant, but there is considerable genetic variation for sensitivity to photoperiod. The critical day length for flowering can range from about 13 hours for genotypes adapted to tropical latitudes to about 24 hours for photoperiod-insensitive genotypes grown at higher latitudes. Soybeans can be insensitive to day length for about 9 days after emergence. It has been observed that photoperiods shorter than the critical day length can be needed for approximately 7 days to approximately 26 days to complete flower induction.

Sensitivity to day length can also be an important consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting (Fehr. 1980. supra). Soybeans frequently are grown in winter nurseries located at sea level in tropical latitudes where day lengths are shorter than their critical photoperiod. The short day lengths and warm temperatures encourage early flowering and seed maturation, and genotypes can produce a seed crop in about 90 days or fewer after planting. Early flowering can be useful for generation advance when only a few self-pollinated seeds per plant are desired, but not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed.

The effect of a short photoperiod on flowering and seed yield can be partly offset by altitude, probably due to the effects of cool temperature. At tropical latitudes, varieties adapted to the northern U.S. perform more like those adapted to the southern U.S. at high altitudes than they do at sea level.

The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. Bot. Gaz. 108:1-26).

Temperature can also play a role in the flowering and development of soybean. It can influence the time of flowering and suitability of flowers for hybridization. Temperatures below about 21° C. or above about 32° C. can reduce floral initiation or seed set (Hammer. 1969. *"Glycine max* (L.) Merrill." In: *The Induction of Flowering: Some Case Histories*. Evans (ed). Ithaca, N.Y.: Cornell University Press, pp. 62-89; van Schaik and Probst. 1978. *Agron. J.* 50:192-197). Artificial hybridization is typically successful between about 26° C. and about 32° C. because cooler temperatures can reduce pollen shed and result in flowers that self-pollinate before they are large enough to manipulate. Warmer temperatures can be frequently associated with increased flower abortion caused by moisture stress; however, successful crosses can be achieved up to about 35° C. if soil moisture is adequate.

Soybeans have been classified as indeterminate, semi-determinate, and determinate based on the abruptness of stem termination after flowering begins. When grown at their latitude of adaptation, indeterminate genotypes flower when about one-half of the nodes on the main stem have developed. They have short racemes with few flowers, and their terminal node has only a few flowers. Semi-determinate genotypes also flower when about one-half of the nodes on the main stem have developed, but node development and flowering on the main stem stops more abruptly than on indeterminates. Their racemes are short and have few flowers, except for the terminal one, which may have several times more flowers than those lower on the plant. Determinate varieties begin flowering when all or most of the nodes on the main stem have developed. They usually have elongated racemes that may be several centimeters in length and may have a large number of flowers. Stem termination and flowering habit are reported to be controlled by two major genes (Bernard and Weiss. 1973. "Qualitative genetics." In: *Soybeans: Improvement, Production and Uses*. Caldwall (ed). Madison, Wis.: Am. Soc. of Agron., pp. 117-154).

Soybean flowers typically are self-pollinated on the day the corolla opens. The amount of natural crossing, which is typically associated with insect vectors such as honeybees, is approximately 1% for adjacent plants within a row and approximately 0.5% between plants in adjacent rows. The structure of soybean flowers is similar to that of other legume species and consists of a calyx with approximately five sepals, a corolla with approximately five petals, approximately ten stamens, and a pistil. The calyx encloses the corolla until the day before anthesis. The corolla emerges and unfolds to expose a standard, two wing petals, and two keel petals. An open flower is about 7 mm long from the base of the calyx to the tip of the standard and about 6 mm wide across the standard. The pistil typically contains a single ovary that contains between one to five ovules, a style that curves toward the standard, and a club-shaped stigma. The stigma is receptive to pollen about 1 day before anthesis and remains receptive for approximately 2 days after anthesis, if the flower petals are not removed. Filaments of nine stamens are typically fused, and the one nearest the standard is typically free. The stamens typically form a ring below the stigma until about 1 day before anthesis, then their filaments begin to elongate rapidly and elevate the anthers around the stigma. The anthers dehisce on the day of anthesis, pollen grains fall on the stigma, and within approximately 10 hours, the pollen tubes reach the ovary and fertilization is completed (Johnson and Bernard. 1963. "Soybean genetics and breading." In: *The Soybean*. Norman (ed) New York: Academic Press, pp. 1-73).

Self-pollination can occur naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is used to remove immature buds that are hidden under the stipules at the leaf axil that can develop into flowers at a later date. Typically, the flower is grasped between the thumb and index finger and the location of the stigma determined by examining the sepals. A long, curvy sepal can cover the keel, and the stigma is typically located on the opposite side of the flower. The calyx is removed by grasping a sepal with the forceps, pulling it down and around the flower, and repeating the procedure until the five sepals are removed. The exposed corolla is removed by grasping it just above the calyx scar, then lifting and wiggling the forceps simultaneously. Care is taken to grasp the corolla low enough to remove the keel petals without injuring the stigma. The ring of anthers is visible after the corolla is removed, unless the anthers were removed with the petals. Cross-pollination can then be carried out using, for example, petri dishes or envelopes in which male flowers have been collected. Desiccators containing calcium chloride crystals are used in some environments to dry male flowers to obtain adequate pollen shed.

It has been demonstrated that emasculation is not necessary to prevent self-pollination (Walker et al. 1979. *Crop Sci.* 19:285-286). When emasculation is not used, the anthers near the stigma can be removed to make the stigma clearly visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, it can be desirable to plant the parents of a cross adjacent to each other. Plants are typically grown in rows about 65 cm to about 100 cm apart to facilitate movement of personnel within a field nursery. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization.

Grafting can be used to hasten the flowering of late flowering genotypes. A scion from a late genotype grafted on a stock that has begun to flower can begin to bloom up to about 42 days earlier than normal (Kiihl et al. 1977. *Crop Sci.* 17:181-182). First flowers on the scion can appear from about 21 days to about 50 days after the graft.

Observing pod development approximately 7 days after pollination is generally sufficient to identify a successful cross. Abortion of pods and seeds can occur several weeks after pollination, but the percentage of abortion is typically low if plant stress is minimized. Pods that develop from artificial hybridization can be distinguished from self-pollinated pods by the presence of the calyx scar, caused by removal of the sepals. The sepals typically begin to fall off as the pods mature; therefore, harvest is preferably completed at or immediately before the time the pods reach their mature color. Harvesting pods early also avoids any loss by shattering.

Once harvested, pods are typically air-dried at not more than approximately 38° C. until the seeds contain approximately 13% moisture or less. The seeds are then removed by hand. Seed can be stored at about 25° C. for up to a year if relative humidity is approximately 50% or less. In humid climates, germination percentage declines rapidly unless the seed is dried to approximately 7% moisture and stored in an air-tight container at room temperature. Long-term storage in any climate is preferably accomplished by drying seed to approximately 7% moisture and storing it at approximately 10° C. or less in a room maintained at about 50% relative humidity or in an air-tight container.

Additional Embodiments of the Invention

Embodiments of the new soybean variety G00-3209 include plants modified to include at least a first desired heritable trait. In some embodiments, such plants can be developed by a plant breeding technique called backcrossing, wherein essentially all of the desired morphological and physiological characteristics of a variety are recovered in addition to a genetic locus transferred into the plant via the backcrossing technique. The term "single locus converted plant" as used herein refers to those soybean plants which are developed by a plant breeding technique called backcrossing, wherein essentially all of the desired morphological and physiological characteristics of a variety are recovered in addition to the single locus transferred into the variety via the backcrossing technique. Backcrossing methods can be used with embodiments of the invention to improve or introduce a characteristic into the new soybean variety G00-3209. The parental soybean plant which contributes the locus for the desired characteristic is termed the "nonrecurrent" or "donor" parent. This terminology refers to the fact that the nonrecurrent parent is used one time in the backcross protocol and therefore does not recur. The parental soybean plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Fehr. 1987. "Principles of variety development." In *Theory and Technique* (*Vol.* 1) and *Crop Species Soybean* (*Vol.* 2). New York: Macmillan Publishing Company, pp. 360-376; Sprague and Dudley, eds. 1988. *Corn and Improvement*, $3^{rd}$ edition).

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

Soybean varieties can also be developed from more than two parents. The technique, known as modified backcrossing, uses different recurrent parents during the backcrossing. Modified backcrossing can be used to replace the original recurrent parent with a variety having certain more desirable characteristics, or multiple parents can be used to obtain different desirable characteristics from each.

Many single locus traits have been identified that are not regularly selected for in the development of a new inbred but that can be improved by backcrossing techniques. Single locus traits can be, but are not necessarily, transgenic. Examples of these traits include, but are not limited to, male sterility, herbicide resistance, resistance to bacterial, fungal, or viral disease, insect resistance, restoration of male fertility, enhanced nutritional quality, yield stability, and yield enhancement. These comprise genes generally inherited through the nucleus.

Direct selection can be applied where the single locus acts as a dominant trait. An example of a dominant trait is the herbicide resistance trait. For the selection process, the progeny of the initial cross are sprayed with a herbicide prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of soybean plants for breeding may not be dependent on the phenotype of a plant and instead can be based on genetic investigations. For example, one can utilize a suitable genetic marker which is closely genetically linked to a trait of interest. One of these markers can therefore be used to identify the presence or absence of a trait in the offspring of a particular cross, and hence can be used in selection of progeny for continued breeding. This technique can commonly be referred to as marker assisted selection. Any other type of genetic marker or other assay which is able to identify the relative presence or absence of a trait of interest in a plant can also be useful for breeding purposes. Procedures for marker assisted selection applicable to the breeding of soybeans are well known in the art. Such methods can be useful in the case of recessive traits and variable phenotypes, or where conventional assays are more expensive, time consuming or otherwise disadvantageous. Types of genetic markers which can be used in accordance with the invention include, but are not necessarily limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Many qualitative characters can also be useful as phenotype-based genetic markers in soybeans; however, some or many may not differ among varieties commonly used as parents (Bernard and Weiss. 1973. supra). Widely used genetic markers include flower color (purple dominant to white), pubescence color (brown dominant to gray), and pod color (brown dominant to tan). The association of purple hypocotyl color with purple flowers and green hypocotyl color with white flowers is commonly used to identify hybrids in the seedling stage. Differences in maturity, height, hilum color, and pest resistance between parents can also be used to verify hybrid plants.

Many useful traits that can be introduced by backcrossing, as well as directly into a plant, are those which are introduced by genetic transformation techniques. Genetic transformation can therefore be used to insert a selected transgene into the soybean variety of the invention or can, alternatively, be used for the preparation of transgenes which can be introduced by backcrossing. Methods for the transformation of many economically important plants, including soybeans, are well know to those of skill in the art. Techniques which can be employed for the genetic transformation of soybeans include, but are not limited to, electroporation, microprojectile bombardment, *Agrobacterium*-mediated transformation and direct DNA uptake by protoplasts.

To effect transformation by electroporation, one can employ either friable tissues, such as a suspension culture of cells or embryogenic callus. Alternatively, one can transform immature embryos or other organized tissue directly. In this technique, one can partially degrade the cell walls of target cells by exposing them to pectin-degrading enzymes (pectolyases) or mechanically wound tissues in a controlled manner.

Protoplasts can also be employed for electroporation transformation of plants (Bates. 1994. *Mol. Biotechnol.* 2(2):135-145; Lazzeri. 1995. *Methods Mol. Biol.* 49:95-106). For example, the generation of transgenic soybean plants by electroporation of cotyledon-derived protoplasts has been described by Dhir and Widholm (WIPO Publication No. WO 1992/017598, which is incorporated herein by reference in its entirety).

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate.

An exemplary embodiment of a method for delivering DNA into plant cells by acceleration is the Biolistics Particle Delivery System, which can be used to propel particles coated with DNA or cells through a screen, such as a stainless steel or Nytex screen, onto a surface covered with target soybean cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

Microprojectile bombardment techniques are widely applicable, and can be used to transform virtually any plant species. The application of microprojectile bombardment for the transformation of soybeans is described, for example, in U.S. Pat. No. 5,322,783, which is incorporated herein by reference in its entirety.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modem *Agrobacterium* transformation vectors are capable of replication in *E. coli* as well as *Agrobacterium*, allowing for convenient manipulations (Klee et al. 1985. Bio. Tech. 3(7):637-342). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is well known in the art (Fraley et al. 1985. *Bio. Tech.*3(7):629-635; U.S. Pat. No. 5,563,055). Use of *Agrobacterium* in the context of soybean transformation has also been described (Chee and Slightom. 1995. *Methods Mol. Biol.* 44:101-119; U.S. Pat. No. 5,569,834, each of which is incorporated herein by reference in its entirety).

Transformation of plant protoplasts can also be achieved using methods based on calcium phosphate precipitation, polyethylene glycol treatment, electroporation, and combinations of these treatments (see, e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189):454-457). The demonstrated ability to regenerate soybean plants from protoplasts makes each of these techniques applicable to soybean (Dhir et al. 1991. *Plant Cell Rep.* 10(2):97-101).

The techniques described above can also be used to introduce transgenes for the production of proteins. The transgene can be harvested from the transgenic plants that are originated or are descended from the new soybean variety G00-3209, a seed of G00-3209 or a hybrid progeny of a G00-3209.

Many hundreds, if not thousands, of different genes are known and can be introduced into a soybean plant according to the invention. Non-limiting examples of particular genes and corresponding phenotypes that can be chosen for introduction into a soybean plant are presented below.

A. Herbicide Resistance

Numerous herbicide resistance genes are known and can be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al. (1988. *The EMBO Journal* 7:1241-1248) and Miki et al. (1990. *Theoretical and Applied Genetics* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes can also be used. See, for example, U.S. Pat. No. 4,940,835, which discloses the nucleotide sequence of a form of EPSPS which can confer glyphosate resistance. Examples of specific EPSPS transformation events conferring glyphosate resistance are described, for example, in U.S. Pat. No. 6,040,497.

A DNA molecule encoding a mutant aroA gene can be obtained under ATCC accession number 39256, and the nucleotide sequence of the mutant gene is disclosed in U.S. Pat. No. 4,769,061. U.S. Pat. No. 4,975,374 discloses nucleotide sequences of glutamine synthetase genes which confer resistance to herbicides such as L-phosphinothricin. The nucleotide sequence of a phosphinothricin-acetyltransferase gene is provided in U.S. Pat. No. 5,879,903. DeGreef et al. (1989. *Bio/Technology* 61-64) describes the production of transgenic plants that express chimeric bar genes coding for phosphinothricin acetyl transferase activity. Exemplary genes conferring resistance to phenoxy propionic acids and cycloshexones, such as sethoxydim and haloxyfop are the Acct-S1, Accl-S2 and Acct-S3 genes described by Marshall et al. (1992. *Theor Appl Genet.* 83:435-442).

Genes conferring resistance to a herbicide that inhibits photosynthesis are also known, such as, for example, a triazine (psbA and gs+genes) and a benzonitrile (nitrilase gene). Przibilla et al. (1991. *Plant Cell.* 3:169-174) describes the transformation of *Chlamydomonas* with plasmids encoding mutant psbA genes. Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes isolation of a gene for dicamba monooxygenase (DMO) from *Pseuodmonas maltophilia* which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known art. The isolation of genes or cloning of plasmids that contribute to the metabolism of such compounds are described, for example, by Müller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

B. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al. (1994. *Science* 266:789) (cloning of the tomato Cf-9 gene for resistance to *Cladosporium fulvum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308), for example, disclose transgenic plants expressing a barley ribosome-inactivating gene have an increased resistance to fungal disease.

C. Insect Resistance

One example of an insect resistance gene includes a *Bacillus thuringiensis* protein, a derivative thereof or a synthetic polypeptide modeled thereon. See, for example, Geiser et al. (1986. *Gene* 48:109), which discloses the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al. (1994. *Plant Mol Biol* 24(5):825-830), which discloses the nucleotide sequences of several *Clivia miniata* mannose-binding lectin genes. A vitamin-binding protein can also be used, such as avidin. See WIPO Publication No. WO 1994/000992, which is incorporated herein by reference in its entirety. This patent publication teaches the use of avidin and avidin homologues as larvicides against insect pests.

Yet another insect resistance gene is an enzyme inhibitor, for example, a protease or proteinase inhibitor or an amylase inhibitor. See, for example, Abe et al. (1987. *J Biol Chem* 262:16793-16797) (nucleotide sequence of rice cysteine proteinase inhibitor), Linthorst et al. (1993) (nucleotide sequence of cDNA encoding tobacco proteinase inhibitor I), and Sumitani et al. (1993. *Plant Molec Biol.* 21:985) (nucleotide sequence of *Streptomyces nitrosporeus*—amylase inhibitor). An insect-specific hormone or pheromone can also be used. See, for example, the disclosure by Hammock et al. (1990. *Nature* 344:458-461), of baculovirus expression of cloned juvenile hormone esterase, an inactivator of juvenile hormone.

Still other examples include an insect-specific antibody or an immunotoxin derived therefrom and a developmental-arrestive protein. See Taylor et al. (1994. *Seventh Intl. Symposium on Molecular Plant-Microbe Interactions* (Edinburgh Scotland), Abstract #497), who described enzymatic inactivation in transgenic tobacco via production of single-chain antibody fragments.

D. Male Sterility

Genetic male sterility is available in soybeans and can increase the efficiency with which hybrids are made, in that it can eliminate the need to physically emasculate the soybean plant used as a female in a given cross. (Brim and Stuber. 1973. *Crop Sci.* 13:528-530). Herbicide-inducible male sterility systems have also been described. (U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the soybean plant is utilized. However, in many cases, the seeds are considered to be a valuable portion of the crop, thus, it is desirable to restore the fertility of the hybrids in these crops. Therefore, embodiments of the invention relate to plants of the new soybean variety G00-3209 comprising a genetic locus capable of restoring male fertility in an otherwise male-sterile plant. Examples of male-sterility genes and corresponding restorers which can be employed with embodiments of the invention are well known to those of skill in the art of plant breeding (see, e.g., U.S. Pat. No. 5,530,191 and U.S. Pat. No. 5,684,242, each of which is incorporated herein by reference in its entirety).

E. Modified Fatty Acid, Phytate and Carbohydrate Metabolism

Genes conferring modified fatty acid metabolism can be used. For example, stearoyl-ACP desaturase genes can be used. See Knutzon et al. (1992. *PNAS* 89:2624-2628). Various fatty acid desaturases have also been described, such as a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al. 1992. *J Biol Chem* 267(9):5931-5936); a gene encoding a stearoyl-acyl carrier protein delta-9 desaturase from castor (Fox et al. 1993. *PNAS* 90(6):2486-2490); Δ6- and Δ12-desaturases from the cyanobacteria *Synechocystis* responsible for the conversion of linoleic acid (18:2) to gamma-linolenic acid (18:3 gamma)

(Reddy et al. 1993. *Plant Mol Biol* 22(2):293-300); a gene from *Arabidopsis thaliana* that encodes an omega-3 desaturase (Arondel et al. 1992. *Science* 258:1353-1355); plant Δ9-desaturases (WIPO Publication No. WO 1991/013972) and soybean and *Brassica* Δ15 desaturases (European Patent Application Publ. No. EP 0616644).

Phytate metabolism can also be modified by introduction of a phytase-encoding gene to enhance breakdown of phytate, adding more free phosphate to the transformed plant. For example, see Van Hartingsveldt et al. (1993. *Gene* 127:87-94), for a disclosure of the nucleotide sequence of an *Aspergillus niger* phytase gene. In soybean, this, for example, could be accomplished by cloning and then reintroducing DNA associated with the single allele which is responsible for soybean mutants characterized by low levels of phytic acid. See Raboy et al. (2000).

A number of genes are known that can be used to alter carbohydrate metabolism. For example, plants can be transformed with a gene coding for an enzyme that alters the branching pattern of starch. See Shiroza et al. (1988. *J Bacteriol* 170(2):810-816) (nucleotide sequence of *Streptococcus* mutants fructosyltransferase gene), Steinmetz et al. (1985. *Mol Gen Genet* 200:220-228) (nucleotide sequence of *Bacillus subtilis* levansucrase gene), Pen et al. (1992. *Bio-Technology* 10:292) (production of transgenic plants that express *Bacillus lichenifonnis*—amylase), Elliot et al. (1993. *Plant Molec Biol* 21:515) (nucleotide sequences of tomato invertase genes), Sorgaard et al. (1993. *J Biol Chem* 268: 22480) (site-directed mutagenesis of barley—amylase gene), and Fisher et al. (1993. *Plant Physiol* 102:1045) (maize endosperm starch branching enzyme II). The Z10 gene encoding a 10 kD zein storage protein from maize can also be used to alter the quantities of 10 kD Zein in the cells relative to other components (Kirihara et al. 1988. *Mol Gen Genet* 211:477-484).

Modifications can include site-specific recombination; abiotic stress tolerance; modified antioxidant characteristics; modified essential seed amino acid characteristics, or the like, or any combination thereof. Merely by way of example, FRT sites and/or Lox sites can be introduced into a soybean plant. FRT sites can be used in the FLP/FRT system. Lox sites can be used in the Cre/Loxp system. Abiotic stress tolerance can include, but not limit to, tolerance to stress induced by, for example, flowering, ear and seed development, enhancement of nitrogen utilization efficiency, altered nitrogen responsiveness, drought resistance or tolerance, cold resistance or tolerance, and salt resistance or tolerance). Such abiotic stress tolerance can increase yield under stress. Modifications can be made to a soybean plant to introduce modified antioxidant characteristics (e.g., content or composition, such as alteration of tocopherol or tocotrienols), modified essential seed amino acid characteristics (e.g. increasing accumulation of essential amino acids in seeds). Exemplary useful genes and traits for transgenic modification of the variety are disclosed in, for example, U.S. Pat. Nos. 7,687,686, 7,649,127 and 7,645,923, each of which is incorporated herein by reference.

Origin and Breeding History of an Exemplary Single Locus Converted Plant

It is known to those of skill in the art that, by way of the technique of backcrossing, one or more traits can be introduced into a given variety while otherwise retaining essentially all of the traits of that variety. An example of such backcrossing to introduce a trait into a starting variety is described in U.S. Pat. No. 6,140,556, which is incorporated herein by reference in its entirety. The procedure described in U.S. Pat. No. 6,140,556 can be summarized as follows: The soybean variety known as Williams '82 [*Glycine max* L. Merr.] (Reg. No. 222, PI 518671) was developed using backcrossing techniques to transfer a locus comprising the $Rps_1$ gene to the variety Williams (Bernard and Cremeens. 1988. *Crop Sci.* 28:1027-1028). Williams '82 is a composite of four resistant lines from the $BC_6F_3$ generation, which were selected from 12 field-tested resistant lines from Williams× Kingwa. The variety Williams was used as the recurrent parent in the backcross and the variety Kingwa was used as the source of the $Rps_1$ locus. This gene locus confers resistance to 19 of the 24 races of the fungal agent phytopthora rot.

The $F_1$ or $F_2$ seedlings from each backcross round were tested for resistance to the fungus by hypocotyl inoculation using the inoculum of race 5. The final generation was tested using inoculum of races 1 to 9. In a backcross such as this, where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent can be composited without the usual replicated tests for traits such as yield, protein or oil percentage in the individual lines.

Tissue Cultures and In Vitro Regeneration of Soybean Plants

Embodiments of the invention also relate to tissue cultures of the new soybean variety G00-3209. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, meristematic cells, pistil, seed, boll, cotyledon, hypocotyl, shoot or stem, and the like. In a preferred embodiment, the tissue culture comprises embryos, protoplasts, meristematic cells, pollen, leaves or anthers.

Exemplary procedures for preparing tissue cultures of regenerable soybean cells and regenerating soybean plants therefrom, are disclosed in U.S. Pat. No. 4,992,375; U.S. Pat. No. 5,015,580; U.S. Pat. No. 5,024,944, and U.S. Pat. No. 5,416,011, each of which is incorporated herein by reference in its entirety.

An important ability of a tissue culture is the capability to regenerate fertile plants. This can allow, for example, transformation of the tissue culture cells followed by regeneration of transgenic plants. For transformation to be efficient and successful, DNA can be introduced into cells that give rise to plants or germ-line tissue.

Soybeans typically are regenerated via two distinct processes; shoot morphogenesis and somatic embryogenesis (Finer et al. 1996. "Soybean transformation: Technologies and progress." In: *Soybean: Genetics, Molecular Biology and Biotechnology*. Verma and Shoemaker (eds). Wallinford, Oxon, UK: CAB International, pp. 250-251). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos, while lines that produce large numbers of embryos during an "induction" step may not give rise to rapidly-growing proliferative cultures. Therefore, it can be desirable to optimize tissue culture conditions for each soybean line. These optimizations can readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it can allow a single, transformed cell to multiply to the point that it can contribute to germ-line tissue.

Shoot morphogenesis was first reported by Wright et al. (1986. *Plant Cell Reports* 5:150-154) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that can give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not give rise to germ-line tissue. Once the system is well understood and reproduced satisfactorily, it can be used as one target tissue for soybean transformation.

Somatic embryogenesis in soybean was first reported by Christianson et al. (1983. *Science* 222:632-634) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck et al. 1988. *In Vitro Cell. Develop. Bio.* 24:821-828). With proliferative embryonic cultures, single cells or small groups of surface cells of the "older" somatic embryos form the "newer" embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells can decrease or eliminate such problems.

Deposit Information

A deposit of 100 packets of seeds of the new soybean variety G00-3209, disclosed above and recited in the claims, has been made with the American Type Culture Collection (ATCC), 10801 University Blvd., Manassas, Virginia 20110. The date of deposit was Apr. 7, 2010. The deposit is intended to meet all of the requirements of 37 C.F.R. §§1.801-1.809. The accession number for those deposited seeds of the new soybean variety G00-3209 is ATCC Accession No. PTA-10783. The deposit will be maintained in the depository for a period of 30 years, or 5 years after the last request, or for the effective life of the patent, whichever is longer, and will be replaced if necessary during that period.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about" or "approximately." For example, "about" or "approximately" can indicate ±20% variation of the value it describes. Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A seed of soybean variety G00-3209, representative seed of said soybean variety having been deposited under ATCC Accession No. PTA-10783.

2. A plant of soybean variety G00-3209, representative seed of said soybean variety having been deposited under ATCC Accession No. PTA-10783.

3. A plant part of the plant of claim 2.

4. The plant part of claim 3, further defined as pollen, an ovule or a cell.

5. A tissue culture of regenerable cells of soybean variety G00-3209, representative seed of said soybean variety having been deposited under ATCC Accession No. PTA-10783.

6. The tissue culture of claim 5, wherein the regenerable cells are from embryos, meristematic cells, pollen, leaves, roots, root tips, anther, pistil, flower, seed, cotyledon, hypocotyl, shoot, protoplasts or stem.

7. A soybean plant regenerated from the tissue culture of claim 5, wherein the regenerated soybean plant expresses all of the physiological and morphological characteristics of the soybean variety G00-3209, representative seed of said soybean variety having been deposited under ATCC Accession No. PTA-10783.

8. A method of producing soybean seed, comprising crossing a plant of soybean variety G00-3209, representative seed of said soybean variety having been deposited under ATCC Accession No. PTA-10783, with itself or a second soybean plant.

9. The method of claim 8, further defined as a method of preparing hybrid soybean seed, comprising crossing a plant of soybean variety G00-3209, representative seed of said soybean variety having been deposited under ATCC Accession No. PTA-10783, with a second, distinct soybean plant.

10. An $F_1$ hybrid seed produced by the method of claim 9.

11. A method of producing a plant of soybean variety G00-3209, representative seed of said soybean variety having been deposited under ATCC Accession No. PTA-10783, comprising an added desired trait, the method comprising introducing a transgene conferring the desired trait into a plant of soybean variety G00-3209.

12. The method of claim 11, wherein the desired trait is selected from the group consisting of: male sterility, herbicide tolerance, insect or pest resistance, disease resistance, site-specific recombination; abiotic stress tolerance; modified phosphorus characteristics; modified antioxidant characteristics; modified essential seed amino acid characteristics; modified fatty acid metabolism, modified carbohydrate metabolism and modified soybean fiber characteristics.

13. The method of claim 12, wherein the desired trait is herbicide tolerance and the tolerance is conferred to an herbicide selected from the group consisting of glyphosate, sulfonylurea, imidazalinone, dicamba, glufosinate, phenoxy proprionic acid, cycloshexone, triazine, benzonitrile, broxynil, and chlorophenoxy acetic acid.

14. The method of claim 11, wherein the desired trait is insect resistance and the transgene encodes a *Bacillus thuringiensis* (Bt) endotoxin.

15. The method of claim 11, wherein the transgene encodes a protein selected from the group consisting of phytase, fructosyltransferase, levansucrase, α-amylase, invertase and starch branching enzyme or encodes an antisense of stearoyl-ACP desaturase.

16. A plant produced by the method of claim 11.

17. A method of introducing a single locus conversion into soybean variety G00-3209 comprising:

(a) crossing a plant of variety G00-3209, representative seed of said soybean variety having been deposited under ATCC Accession No. PTA-10783, with a second plant comprising a desired single locus to produce $F_1$ progeny plants;

(b) selecting $F_1$ progeny plants that have the single locus to produce selected $F_1$ progeny plants;

(c) crossing the selected progeny plants with at least a first plant of variety G00-3209 to produce backcross progeny plants;

(d) selecting backcross progeny plants that have the single locus and physiological and morphological characteristics of soybean variety G00-3209 to produce selected backcross progeny plants; and (e) repeating steps (c) and (d) one or more times in succession to produce selected second or higher backcross progeny plants that comprise the single locus and the physiological and morphological characteristics of soybean variety G00-3209 when grown in the same environmental conditions.

18. The method of claim 17, wherein the single locus confers a trait selected from the group consisting of male sterility; herbicide tolerance; insect or pest resistance; disease resistance; site-specific recombination; abiotic stress tolerance; modified phosphorus characteristics; modified antioxidant characteristics; modified essential seed amino acid characteristics; modified fatty acid metabolism; modified carbohydrate metabolism; and modified soybean fiber characteristics.

19. The method of claim 18, wherein the trait is tolerance to an herbicide selected from the group consisting of glyphosate, sulfonylurea, imidazalinone, dicamba, glufosinate, phenoxy proprionic acid, cycloshexone, triazine, benzonitrile, broxynil, and chlorophenoxy acetic acid.

20. The method of claim 18, wherein the trait is insect resistance and the insect resistance is conferred by a transgene encoding a *Bacillus thuringiensis* endotoxin.

21. A plant of soybean variety G00-3209, representative seed of said soybean variety having been deposited under ATCC Accession No. PTA-10783, further defined as comprising a single locus conversion.

22. The plant of claim 21, wherein the single locus is introduced into the plant by backcrossing or genetic transformation.

23. A method of producing an inbred soybean plant derived from the soybean variety G00-3209, the method comprising the steps of:

(a) preparing a progeny plant derived from soybean variety G00-3209, representative seed of said soybean variety having been deposited under ATCC Accession No. PTA-10783, by crossing a plant of the soybean variety G00-3209 with a soybean plant of a second variety;

(b) crossing the progeny plant with itself or a second plant to produce a seed of a progeny plant of a subsequent generation;

(c) growing a progeny plant of a subsequent generation from said seed and crossing the progeny plant of a subsequent generation with itself or a second plant; and (d) repeating steps (b) and (c) for an additional 3-10 generations with sufficient inbreeding to produce an inbred soybean plant derived from the soybean variety G00-3209.

24. A method of producing a commodity plant product comprising obtaining the plant of claim 2 or a part thereof and producing said commodity plant product therefrom.

25. The method of claim 24, wherein the commodity plant product is protein concentrate, protein isolate, soybean hulls, meal, flour or oil.

* * * * *